US008424064B2

(12) United States Patent
Gardcia et al.

(10) Patent No.: US 8,424,064 B2
(45) Date of Patent: Apr. 16, 2013

(54) DISTRIBUTED DEVICE REVOCATION (75) Inventors: Oscar Gardcia, Aachen (DE); Heribert Baldus, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 587 days.

(21) Appl. No.: 12/447,007

(22) PCT Filed: Oct. 31, 2007

(86) PCT No.: PCT/US2007/083076
§ 371 (c)(1),
(2), (4) Date: Apr. 24, 2009

(87) PCT Pub. No.: WO2008/055191
PCT Pub. Date: May 8, 2008

(65) Prior Publication Data
US 2010/0031318 A1 Feb. 4, 2010

Related U.S. Application Data (60) Provisional application No. 60/864,026, filed on Nov. 2, 2006.

(51) Int. Cl.
H04L 9/00 (2006.01)
(52) U.S. Cl.
USPC .................................. 726/4; 713/158; 705/71
(58) Field of Classification Search ...... 726/4; 713/158; 705/71
See application file for complete search history.

(56) References Cited

U.S. PATENT DOCUMENTS

| | | | | |
|---|---|---|---|---|
| 6,735,630 | B1 * | 5/2004 | Gelvin et al. | 709/224 |
| 7,350,069 | B2 * | 3/2008 | Herz et al. | 713/150 |
| 7,382,762 | B2 * | 6/2008 | Chmora et al. | 370/342 |
| 7,756,924 | B2 * | 7/2010 | Kaler | 709/204 |
| 2005/0140964 | A1 | 6/2005 | Eschenauer et al. | |
| 2007/0220116 | A1 * | 9/2007 | Rose | 709/219 |

OTHER PUBLICATIONS

Chan et al., "On the Distribution and Revocation of Cryptographic Keys in Sensor Networks", Jul.-Sep. 2005, IEEE transactions on dependable and secure computing, vol. 2, pp. 233-247.*
"On the Distribution and Revocation of Cryptographic Keys in Sensor Networks", Jul.-Sep. 2005, IEEE transactions on dependable and secure computing, vol. 2, pp. 233-247.*
Crepeau, C., et al.; A Certificate Revocation Scheme for Wireless Ad Hoc Networks; 2003; Proc. 1st ACM Workshop on Security of Ad Hoc and Sensor Networks; pp. 54-61.
Chan, H., et al.; Random Key Predistribution Schemes for Sensor Networks; 2003; IEEE Symposium on Security and Privacy; pp. 197-213.

(Continued)

Primary Examiner — Jason K. Gee
Assistant Examiner — Thomas Ho (57) ABSTRACT

In a distributed revocation method, it is individually decided at each of a plurality of autonomous device nodes of a distributed network whether a suspect autonomous device node or suspect distributed key of the distributed network should be removed from the distributed network. A voting session is conducted at which the individual decisions of the plurality of autonomous device nodes are combined to decide whether the suspect autonomous device node or suspect distributed key should be removed from the distributed network. The suspect autonomous device node or suspect distributed key is removed from the distributed network responsive to the voting session deciding in favor of removal.

26 Claims, 5 Drawing Sheets

OTHER PUBLICATIONS

Chan, H., et al.; On the Distribution and Revocation of Cryptographic Keys in Sensor Networks; 2005; IEEE Trans. on Dependable and Secure computing; 2(3)233-247.

Zhu, S., et al.; LEAP: Efficient Security Mechanisms for Large-Scale Distributed Sensor Networks; 2003; Proc. 10th ACM Conf. on Computer and Communication Security; pp. 62-72.

* cited by examiner

DISTRIBUTED DEVICE REVOCATION

The following relates to the distributed data acquisition, processing, and related arts. It especially relates to security of distributed networks of wirelessly intercommunicating medical devices configured to monitor vital signs or other diagnostically significant physiological parameters of a medical patient, provide controlled drug delivery to the patient, providing flow-controlled intravenous fluid delivery to the patient, or so forth, and is described with particular reference thereto. The following relates more generally to security of distributed networks of any sort, whether connected wirelessly or by wired connections, of autonomous device nodes configured to perform medical applications, control applications (such as for example control of distributed building lights or climate control registers), or so forth. In another generalized aspect, the following relates generally to security of distributed networks in which autonomous device nodes are capable of being added and removed in an ad hoc manner, such as Bluetooth networks of electronic devices, WiFi hotspots at which laptop computers or other WiFi-capable devices may connect and disconnect in an ad hoc manner, distributed peer-to-peer file-sharing networks, and so forth.

Autonomous wirelessly interconnected medical devices are increasingly being used in hospitals and other medical facilities. Such devices eliminate wired communication connections such as cables and leads which otherwise impede movement of medical personnel and the patient. Such wireless autonomous medical devices can be interconnected to form an ad hoc distributed network, which facilitates adding and removing medical devices in accordance with the changing medical situation of the patient. The use of wireless autonomous devices interconnected as a distributed network can also provide efficient distribution of computing resources, enhanced redundancy in the event of failure of a device, redundancy in data storage that can be advantageous if one device loses its memory contents, and so forth.

Distributed networks implicate substantial security concerns. Each autonomous device represents a potential point for compromising security of the distributed network. A consequence of the autonomous nature of the devices is that any individual device can, in principle, be taken over by malicious software (e.g., a virus, Trojan horse, worm, or so forth). Once an intruder takes over one of the autonomous devices, the intruder can use the compromised device to disrupt the distributed network or steal medical data. The importance placed on maintaining the integrity and privacy of patient medical data is evidenced by legal protections given to medical data by, for example, the Health Insurance Portability and Accountability Act (HIPAA) passed in the United States in 1996. If the distributed network includes devices that provide therapy to the patient (such as intravenous flow meters, drug delivery systems, or so forth) such a compromising of the distributed network can even be used to directly harm the patient.

Two ways of ensuring security of a network are (1) preventing any node from being compromised, or (2) detecting a compromised node and excluding it from the network. The second option is addressed herein. In this latter approach, a compromised node is detected and its network privileges are revoked, thus isolating the compromised node from the network. This approach limits the damage that can be done by the compromised node to those areas under direct control of the compromised node.

In a centralized network, a central server node controls communication and has authority over the other nodes of the network. Hence, in a centralized network, revocation of any given node (except the central server node) is straightforward and merely involves having the dominant central server node revoke the network privileges of the compromised node. In a distributed network, however, revocation is more difficult because there is no central node configurable to authorize revocations. At the same time, the autonomous nature of the devices of the distributed network enhances the risk involved when a single node is compromised, because a compromised node is not under centralized control and is relatively more free to perform malicious or destructive acts.

In accordance with one aspect, a distributed revocation method is disclosed, including: conducting a vote amongst at least three autonomous device nodes of a distributed network regarding whether a suspect autonomous device node of the distributed network should be removed from the distributed network, and, responsive to said vote satisfying a revocation criterion, ceasing communication between the suspect autonomous device node and the other autonomous device nodes of the distributed network by constructing a revocation message by combining partial revocation information for revoking the suspect autonomous device node that is distributed amongst at least some of the autonomous device nodes of the distributed network other than the suspect autonomous device node, intercommunicating the revocation message amongst the autonomous device nodes of the implicated distributed network, and, optionally, forwarding the revocation message to other autonomous device nodes in other distributed networks.

In accordance with another aspect, a distributed network is disclosed, including a plurality of autonomous device nodes each configured to securely communicate with other autonomous device nodes to define the distributed network and to cooperate with other autonomous device nodes with which it is in secure communication to perform the distributed revocation method of the preceding paragraph.

In accordance with another aspect, an autonomous device node is disclosed, that is configured to securely communicate with other autonomous device nodes in a distributed network and to cooperate with other autonomous device nodes with which it is in secure communication to perform a distributed revocation method including (i) conducting a vote amongst at least three autonomous device nodes of a distributed network regarding whether a suspect autonomous device node of the distributed network should be removed from the distributed network, the vote being weighted based on a trust factor indicative of trustworthiness of the suspect autonomous device node in the distributed network, and (ii) ceasing communication with the suspect autonomous device node responsive to said vote satisfying a revocation criterion.

In accordance with another aspect, a distributed revocation method is disclosed, including: conducting a temporally limited revocation session at which individual decisions of a plurality of autonomous device nodes are combined to decide whether a suspect autonomous device node should be removed from a distributed network; and removing the suspect autonomous device node from the distributed network responsive to the revocation session deciding in favor of removal.

In accordance with another aspect, an autonomous device node is disclosed, that is configured to securely communicate with other autonomous device nodes in a distributed network and to cooperate with other autonomous device nodes with which it is in secure communication to perform the distributed revocation method as set forth in the preceding paragraph.

In accordance with another aspect, a plurality of nodes are disclosed in a distributed medical monitoring network. Each node is programmed to confer and decide democratically with other nodes of the network whether to revoke network communication with a node detected engaging in one or more suspicious activities.

In accordance with another aspect, a distributed network comprising a plurality of nodes is disclosed. Each node is configured to: (i) randomly generate and distribute to other nodes partial revocation votes combinable to construct a revocation message against the node such that the partial revocation vote distributed to one other node cannot be replicated or forged by another node; and (ii) store partial revocation votes received from other nodes.

One advantage resides in enhancing the security of a distributed network by providing for revocation of network privileges of a suspect autonomous device node.

Another advantage resides in inhibiting a compromised autonomous device node of a distributed network from interfering with its revocation from the network.

Another advantage resides in reducing a likelihood that a properly functioning autonomous device node or distributed key of a distributed network will be improperly removed from the distributed network.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

Figure 1:
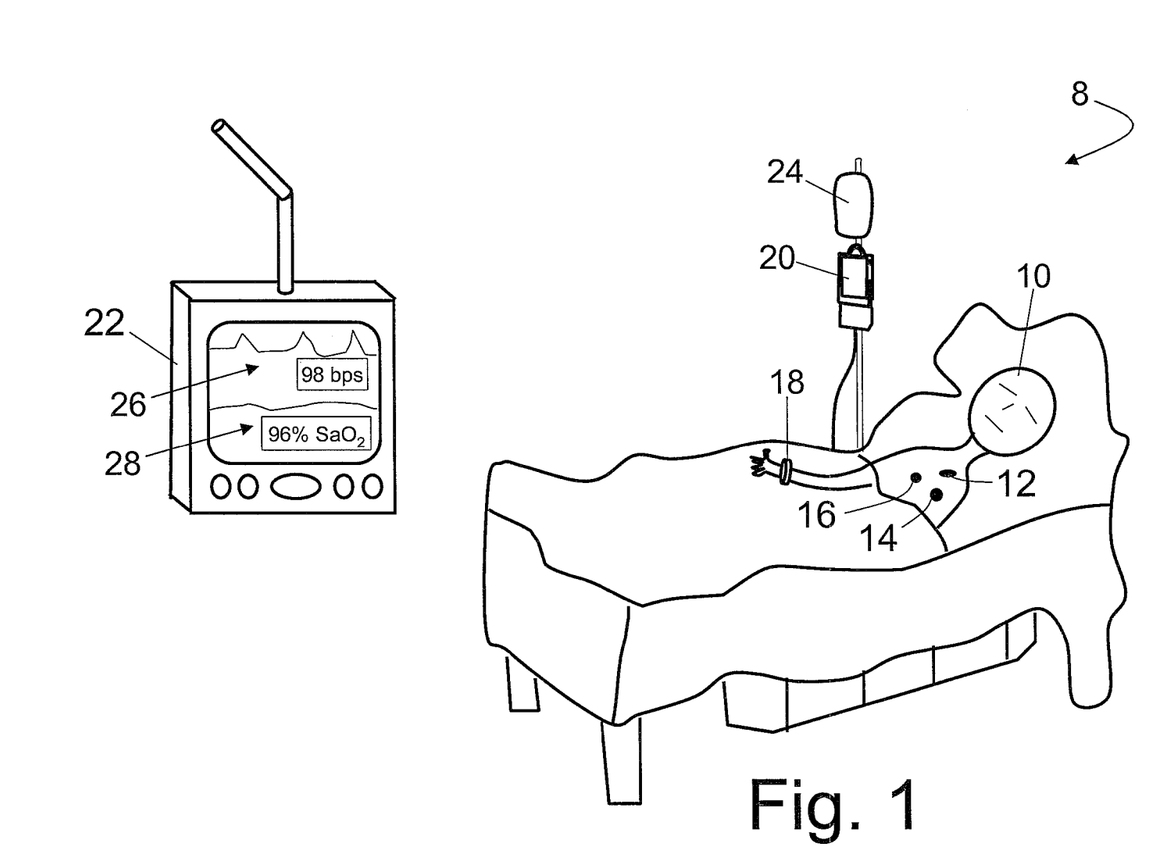
FIG. 1 diagrammatically shows a distributed network of medical devices for monitoring and treating a patient, in which the devices are configured to perform a distributed device revocation method.

With reference to FIG. 1, in an example application of a distributed network 8, a medical patient 10 is monitored and, optionally, treated. The distributed network 10 includes a plurality of autonomous device nodes, such as the example illustrated chest-mounted sensors 12, 14, 16, wrist-mounted sensor 18, intravenous (IV) fluid drip flow meter 20, and ceiling-mounted external display monitor 22. The autonomous device nodes 12, 14, 16, 18, 20, 22 perform various medical functions, such as: monitoring of vital signs or other diagnostically significant physiological parameters of the patient 10 performed by the chest- and wrist-mounted sensors 12, 14, 16, 18; performing therapy functions such as delivering a flow of intravenous fluid from an IV bag 24 to the patient 10 controlled by the flow meter 20; performing auxiliary tasks such as display by the display monitor 22 of vital sign data acquired by the sensors 12, 14, 16, 18; and so forth. The example display of the monitor 22 is showing pulse information 26 suitably acquired by one of the chest-based sensors 12, 14, 16, and blood oxygenation (SpO$_2$) data 28 acquired by the wrist-mounted sensor 18.

The autonomous device nodes 12, 14, 16, 18, 20, 22 are wireless devices that intercommunicate by a suitable wireless protocol such as Bluetooth, Zigbee, WiFi, or so forth. Alternatively, wired devices that intercommunicate via a wired network such as a wired Ethernet network may be used, although wired configurations have the disadvantage of cabling that can impede movement of medical personnel or the patient. The autonomous device nodes 12, 14, 16, 18, 20, 22 are autonomous in that each device can operate independent of centralized control. However, in some cases an autonomous device may lose some functionality when disconnected from certain other devices. For example, the sensors 12, 14, 16, 18 may have limited data storage and little or no display capability. Ordinarily, these sensors 12, 14, 16, 18 operate in conjunction with the display monitor 22 which provides a large-area display for showing trending data and so forth, and may also have a larger data storage. If the patient 10 moves, or is moved, out of the room such that the sensors 12, 14, 16, 18 are moved out of wireless contact with the ceiling-mounted monitor 22, then the display monitor 22 temporarily drops out of the distributed network 8, and the sensors 12, 14, 16, 18 lose some of their functionality, However, the autonomous sensors 12, 14, 16, 18, continue to operate at a reduced functionality level in the distributed network 8 to acquire and store data at least until the on-board memory is exhausted. Optionally, the data acquisition rate, resolution, or other parameters may be altered in such a case to reduce the rate of memory usage. Similarly, the IV flow meter 20 may typically be in contact with the hospital network so as to provide the nurses' station with information on the status of the IV feed. If the patient moves, or is moved, outside of the range of the hospital network, then this functionality of communicating with the nurses' station is lost. In this reduced functionality state, however, the autonomous flow meter 20 continues to operate to regulate flow of IV fluid to the patient 10. The distributed network 8 is an ad hoc network in which device nodes may join or drop out at various times. However, discussed herein, certain protocols relating to the distributed device revocation system are requisite to a new device node joining the distributed network 8.

Each autonomous device node typically corresponds to an autonomous device, although this is not always the case. For example, in some cases a single autonomous device may define two or more device nodes, such as in the case of a single computer that concurrently executes two or more virtual machines.

The distributed network 8 is an ad hoc network in which devices may be added or removed as dictated by the patient's condition, patient's location, patient's course of treatment, availability of devices, and so forth. For example, in FIG. 1 the ceiling-mounted display monitor 22 is part of the distributed network 8; however, if the patient moves, or is moved, out of the room and out of range of the display monitor 22, then the display monitor 22 will drop out of the distributed network 8, at least until the patient 10 moves or is moved back into wireless communication range.

To maintain the security and integrity of the distributed network 8, a suitable security protocol is employed. This protocol includes employing key-protected communication protocols in which autonomous devices of the distributed network 8 accept data only from other autonomous devices of the distributed network 8 that include the appropriate authentication key or other appropriate authentication information. Such authentication can be based on security keys such as those of a hierarchical deterministic pairwise key pre-distribution scheme (HDPKPS), or public/private key pairs, or so forth or substantially any other type of secured communication.

The autonomous nature of the autonomous device nodes 12, 14, 16, 18, 20, 22 of the distributed network 8 presents an additional security concern. One of the autonomous device nodes may be compromised, for example, by being infected by a malignant virus or other malicious software code, or by being logged into by an unauthorized person, or so forth. Such a compromised autonomous device node will continue to be configured for authorized communication with other autonomous device nodes of the distributed network 8, in that it will continue to communicate using the recognized public/private key pair protocol or other secure communication protocol. Thus, such a compromised device presents a substantial security threat.

Accordingly, the autonomous device nodes 12, 14, 16, 18, 20, 22 of the distributed network 8 additionally cooperatively execute a distributed revocation method that enables a compromised autonomous device to be excluded from the autonomous network 8. To ensure that the compromised device cannot use the distributed revocation method against uncompromised devices, the revocation method includes democratic interaction amongst the device nodes. If a vote against a suspect device satisfies a revocation criterion, then the uncompromised devices cease communication with the suspect and revoked autonomous device. Assuming that most of the autonomous devices are not compromised, this distributed revocation approach ensures that the compromised autonomous device cannot revoke uncompromised devices, and cannot thwart its own revocation, because it will be outvoted by the uncompromised devices.

Figure 2:
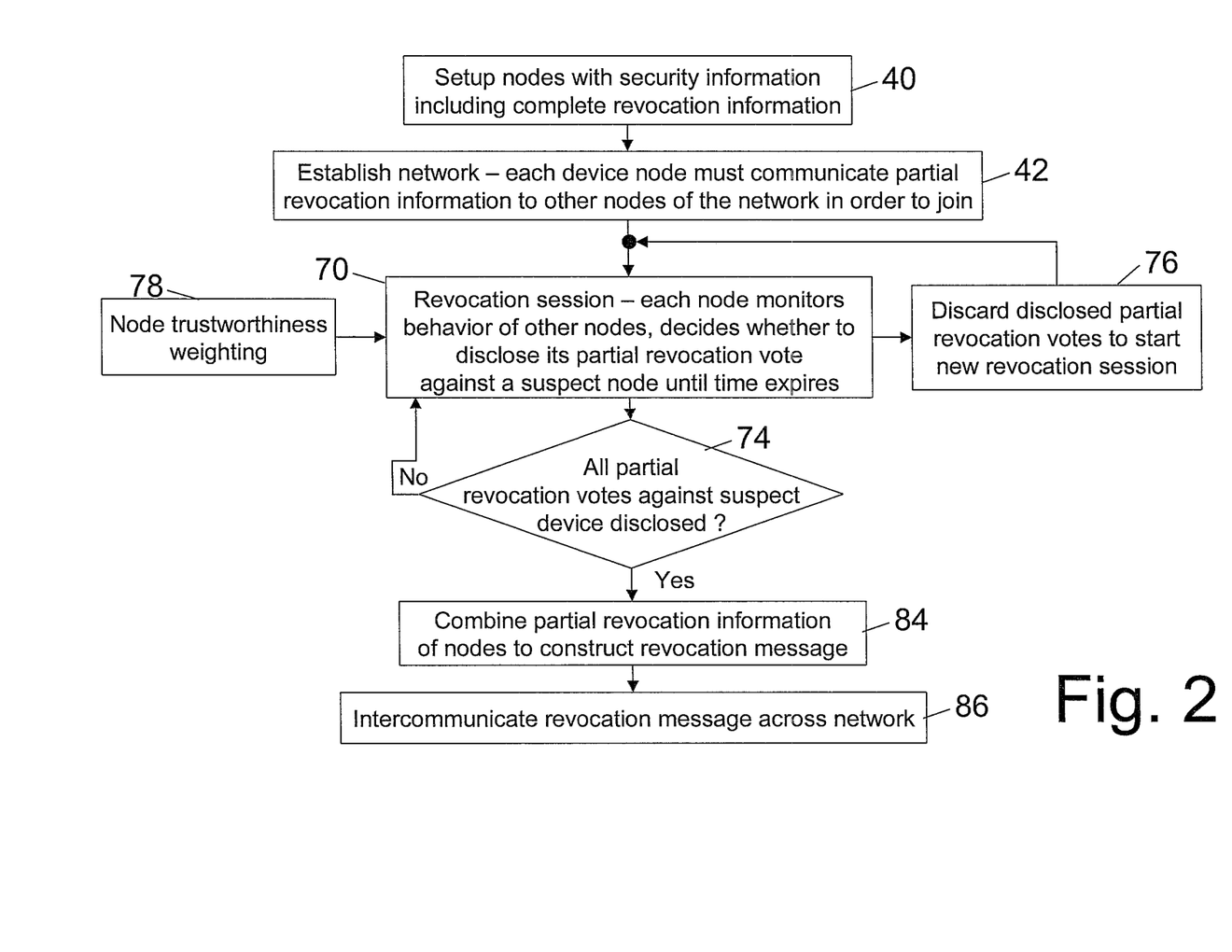
FIG. 2 diagrammatically shows a distributed device revocation method suitably performed by the distributed network of FIG. 1 or by another distributed network.

With reference to FIG. 2, the distributed revocation process is described. In a setup operation 40, each of the autonomous nodes 12, 14, 16, 18, 20, 22 is configured with security information enabling secure intercommunication. For example, a key management scheme may be employed that provides and manages cryptographic keys to enable security services such as authentication, confidentiality and integrity. The key management scheme operating in conjunction with the example revocation system includes two components; key distribution and key revocation. Key distribution describes how to distribute secret information among autonomous nodes to bootstrap a secure communication. The distributed revocation method enables revocation of suspect autonomous nodes that have been compromised, or manifest indications of possible compromise, in an authenticated way.

The features of the distributed revocation approaches disclosed herein exhibit some or all of the following features. First, the revocation approach is a distributed revocation approach. The distributed network 8 is an ad hoc network having no centralized server or controller node, thus making a distributed revocation approach advantageous. Second, the distributed revocation approach utilized collaboration of autonomous nodes of the distributed network 8. The autonomous nodes 12, 14, 16, 18, 20, 22 cooperate to discover and expel compromised, or apparently compromised, autonomous nodes from the distributed network 8 in a democratic way. Third, the revocation is authenticated. The distributed device revocation method enables any sufficiently large subset of autonomous device nodes to agree on the revocation of any suspect autonomous device node before such revocation occurs. To avoid misuse of the revocation system to exclude properly operating autonomous device nodes, a revocation message is constructed by at least those devices voting to expel the suspect autonomous device node, and this revocation message is configured to be authenticated at any autonomous device node in the distributed network 8 so that the device node can verify the veracity of a revocation message against the suspect autonomous device node.

Fourth, the revocation method optionally employs weighting based on trustworthiness of the suspect device. Trust among autonomous device nodes may differ. As an example in the medical field, consider a group of autonomous sensor devices monitoring vital signs of a patient. If a new sensor that is substantively different (e.g., not a sensor device) requests permission to join to the network, the sensor device nodes may distrust it. If device nodes already in the network distrust the new candidate node, then the revocation should weight the new node by a trustworthiness factor selected to enhance the likelihood of revocation. Accordingly, in some embodiments the device revocation approach includes different trustworthiness factors for different nodes indicative of differing levels of trust among nodes, so as to build a flexible weighted revocation scheme.

A fifth optional feature relates to robustness of the distributed revocation approach. Any given autonomous node may exhibit occasional behavior that might be viewed as suspect by another node. For example, an autonomous sensor device node might communicate an erroneous measurement due to a glitch, or might communicate a legitimate measurement that is outside of the expected range for that measurement. Such behavior may cause the recipient autonomous node to conclude that the sending node has been compromised, causing the recipient node to vote for revocation of the sending node. Over time, it will be appreciated that such occasional unusual behavior may accumulate to the point where a sufficient number of votes for revocation accumulate to cause the revocation system to exclude a properly functioning device node that has not been compromised but that exhibits occasional aberrant behavior. To address this possibility, the distributed revocation system optionally uses temporally limited revocation sessions, and each vote is based on behavior observed during the temporally limited revocation session. This approach avoids accumulation of occasional aberrant behavior over prolonged periods of time leading to improper revocation. A revocation session is a period of time that limits the validity of the revocation information against a device.

The distributed revocation approach of FIG. 2 is divisible into two phases, namely a pre-deployment phase embodied by the setup operation 40, and a post-deployment phase. In the pre-deployment phase or setup operation 40, a server or other setup controller (not shown) generates and distributes security keying material or other security material to each autonomous device node to be incorporated into the distributed network. The distributed security material includes revocation information for each device node that enables device revocation during the post-deployment phase.

In a network establishment operation 42, each autonomous device node seeking to join the distributed network interacts with at least some other device nodes by distributing revocation information to the other nodes. The successful distribution of such revocation information is a prerequisite to establish communication with the distributed network. Accordingly, every autonomous device node disseminates revocation information to the other device nodes of the distributed network. The network establishment operation 42 may include other operations as well, such as exchange of public keys to enable secure communication, determination of mutually compatible communication protocols, and so forth. At the end of the establishment operation 42, the distributed network 8 is established, and each autonomous node has distributed its revocation information amongst at least some other autonomous nodes of the distributed network.

Some suitable authentication approaches for authenticating votes and revocation messages employ one-way functions. For example, a hash function h may be used which has at least the following two properties: (i) a compression property in which the hash function h maps an input x of arbitrary finite bit length to an output h(x) of fixed bitlength n; and (ii)

an ease of computation property in that, given h and an input x, h(x) is easy to compute. A one-way hash function is a hash function for which finding an input that hashes to a pre-specified hash-value is difficult. In general a one-way hash function has pre-image and second pre-image resistance.

Figure 3:
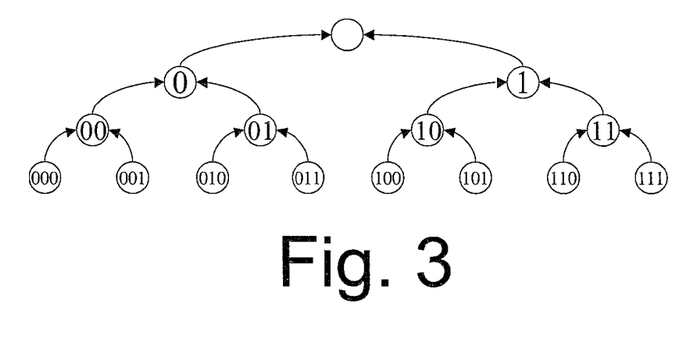
FIG. 3 diagrammatically shows a binary tree.

With brief reference to FIG. 3, binary trees may also be used in authentication. A complete binary tree T of height H has $2^H$ leaves and $2^H-1$ interior nodes. As shown in the diagrammatic example of FIG. 3 (where in this example H=3), each interior node has two children labeled "0" (left), and "1" (right), and the leaf nodes are each labeled by three bits, e.g. "000", "001", and so forth. With this naming convention the leaves are naturally ordered and indexed according to the binary representation of the path from the root to the leaf as shown in FIG. 3.

Figure 4:
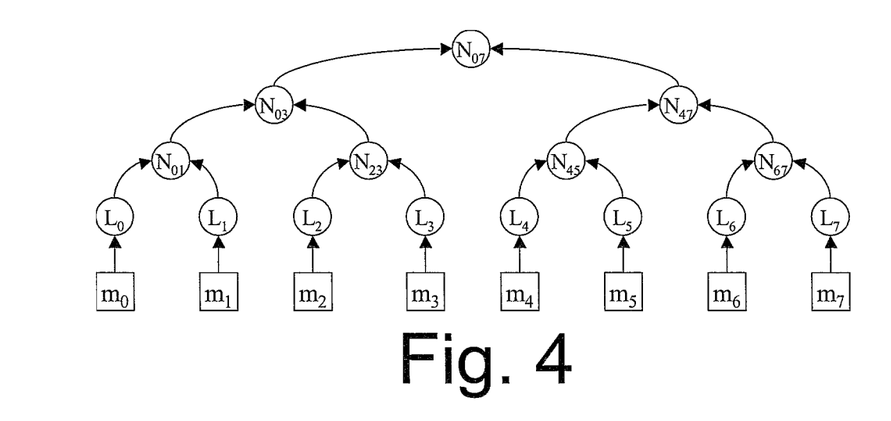
FIG. 4 diagrammatically shows a Merkle tree.

With brief reference to FIG. 4, a Merkle tree of height H is a binary tree with an assignment of a string of l bits to each interior node and leaf. Strings are determined as follows: (i) leaf values ($L_j$, j=0, ..., $2^H-1$) are the one-way hash functions of some leaf pre-image ($m_j$), such that $L_a$=h($m_a$); and (ii) interior nodes are one-way hash functions of either the children's nodes or leaves such that $N_{ad}$=h($N_{ab}$||$N_{cd}$) or $N_{ad}$=h($L_a$||$L_d$). A Merkle tree is useable to authenticate pre-image values in an efficient way—to authenticate $2^H$ pre-images only H values and hash computations are required. For example, to authenticate $m_0$ respective to the Merkle tree shown in FIG. 4, one computes h(h(h(h($m_0$)||$L_1$)||$N_{23}$)||$N_{47}$) and compares the result with the tree root $N_{07}$.

A modified authentication Merkle tree (MAMT) is suitably used to identify the path in a Merkle tree. Toward this end, strings are determined as follows: (i) interior nodes (corresponding to the nodes labeled $N_{xy}$ in FIG. 3) are given by $N_{ad}$=h(a||$N_{ab}$||$N_{cd}$||d) or by $N_{ad}$=h(a||$L_a$||$L_d$||d); and (ii) leaf nodes (corresponding to the nodes labeled "$L_i$", i=0 ... 7 in FIG. 3) are given by $L_a$=h(a||$m_a$). The use of a MAMT also prevents birthday attacks.

With these definitions, a hash chain of the form ($m^1$, ..., $m^s$) is defined, which is a collection of values such that each value $m^k$ (except the last value $m^s$) is a one-way hash function of the next value. That is, $m^{k+1}$=h($m^k$) where h( ) is a one-way has function. In some embodiments, given element (k+1)th of a hash chain, element m^(k+1)th, is calculated as m^(k+1)=h(k||m^k). The construction of a hash chain in this way advantageously avoids birthday attacks.

With returning reference to FIG. 2, the nodes setup operation 40 generates the distributed device revocation system keying material. In the example embodiment, this material includes revocation information, sometimes also called partial revocation values or votes herein. This information is the information that is disclosed to neighboring autonomous device nodes are part of the network setup. Neighboring autonomous device nodes can collaboratively exploit the partial revocation voting information to revoke a suspect autonomous device node. In general each autonomous device node owns t(s+1) partial revocation votes, where t refers to the number of partial revocation votes for each revocation session and (s+1) refers to the number of revocation sessions. In the example embodiment, partial revocation values for each autonomous device node are composed of a collection of t random revocation values as well as t hash chains of length s generated from each random revocation value.

During a revocation session, if a vote is taken that concludes in favor of revoking a suspect autonomous device node, then a revocation vote or revocation message is generated that unambiguously indicates that the suspect autonomous device node is to be revoked. Such a revocation vote or message unambiguously determines that the suspect autonomous device node is to be revoked in revocation session k, and can only be generated by exploiting the partial revocation votes or information of the $k^{th}$ revocation session for the suspect device node that have been previously distributed to other device nodes during the network setup 42.

In the example embodiment, the distributed device revocation system keying material further includes partial revocation votes MAMT used to authenticate partial revocation votes or information, and the revocation vote MAMT used to authenticate the revocation vote or information. The partial revocation votes MAMT includes two MAMT's used to authenticate partial revocation votes: (i) a first MAMT is the revocation authentication tree (RAT, also sometimes denoted herein as the partial revocation vote authentication tree $PM_i$ for device i) used to authenticate the partial revocation votes of a device node, and (ii) a second MAMT is the global revocation authentication tree (GRAT, also sometimes denoted herein as the global partial revocation vote authentication tree GPM) used to authenticate the RAT of all network devices. The revocation vote MAMT is composed of two additional MAMT whose function is to authenticate the revocation vote or information of a device node.

Figure 5:
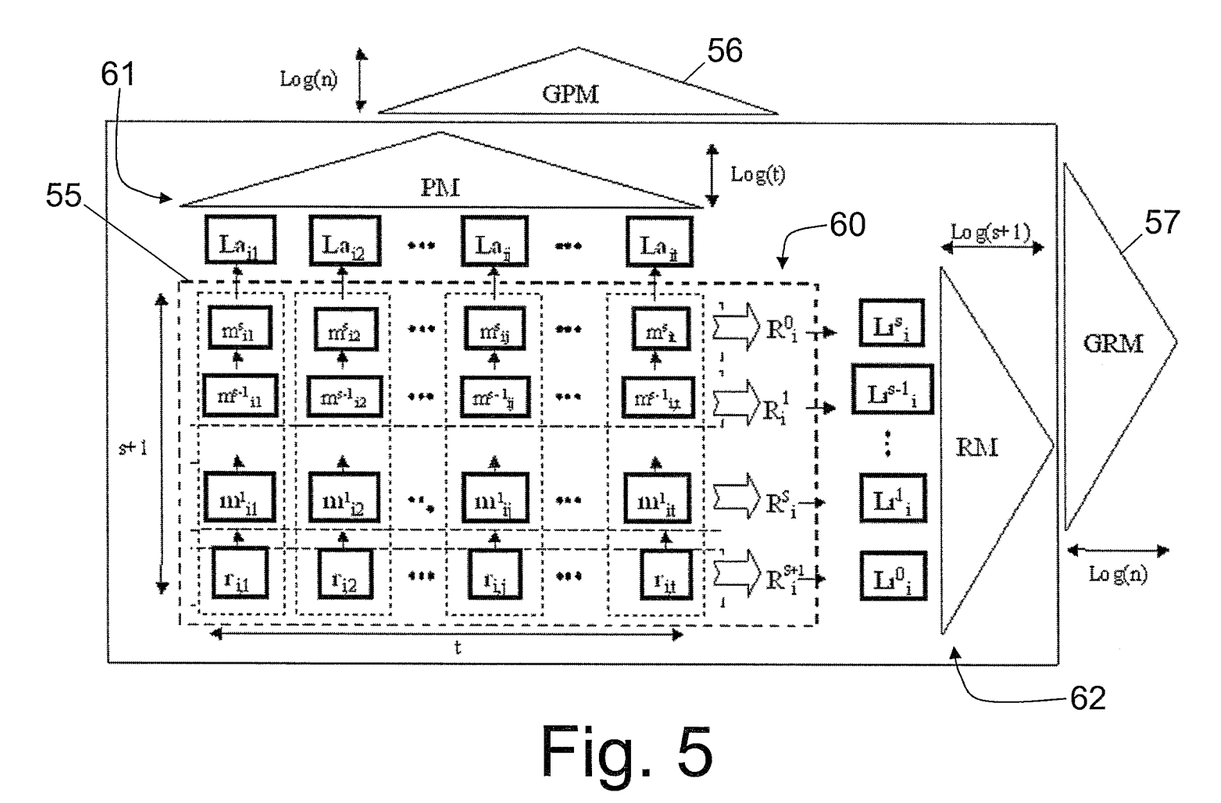
FIG. 5 diagrammatically shows an illustrative distributed device revocation system data structure.

With continuing reference to FIG. 2 and with further reference to FIG. 5, in the example embodiment, the distributed device revocation system keying material is generated during the nodes setup 40 as follows. Keying material generation has two main stages: (i) keying material generation for each device, and (ii) global MAMT generation. FIG. 5 depicts the generated distributed device revocation system keying material for an autonomous device node 55 as well as both global MAMT 56, 57.

In the first stage, keying material is generated for each device node. Generation of the partial revocation vote information is as follows. A set of random revocation votes is generated. Each random revocation vote has length l bits and is identified by $r_{ij}$, where i identifies the device and j identifies the $j^{th}$ random revocation vote in a device node. In FIG. 5 the random revocation votes for device i are situated in the last row of the distributed device revocation system information for the autonomous device node 55. For each random revocation vote $r_{ij}$, a setup server (not shown) generates a hash chain of length s. Hash elements are called hash revocation votes herein and are denoted by $m_{i,j}^k$, where i identifies the device node and k and j identify the $j^{th}$ hash revocation vote in a device node for revocation session k. The hash revocation votes are generated from the random revocation votes as follows: $m_{i,j}^1$=h($r_{i,j}$), $m_{i,j}^2$=h($m_{i,j}^1$), and, generalizing to the $s^{th}$ value, $m_{i,j}^s$=h($m_{i,j}^{s-1}$). In FIG. 5, the hash revocation votes $m_{i,j}^k$ are symbolized by t columns of s elements within of the distributed device revocation system keying material for an autonomous device node 55.

The revocation values or information are generated as follows. The setup includes generation of s+1 revocation values denoted $R_i^k$ where i identifies the device node and k identifies the $k^{th}$ revocation session. These values are given by: $R_i^0$=h ($r_{i,1}$||$r_{i,2}$|| ... ||$r_{i,t}$) for the k=0 value and by $R_j^{s-k}$= h($m_{i,1}^k$||$m_{i,2}^k$|| ... ||$m_{i,t}^k$) for the k=1, ... s. In FIG. 5 revocation values 60 are shown on the right side of the distributed device revocation system keying material for an autonomous device node 55.

Computation of the partial revocation votes MAMT is as follows. This MAMT authenticates the partial revocation votes a device node has. The partial revocation vote MAMT for device i has t leaves denoted $La_{i,j}$ for j=1, ..., t. Each leaf is calculated as $La_{i,j}$=h(j||$m_{i,j}^s$). The root for the partial revocation votes MAMT for device i is denoted herein as $PM_i$. The partial revocation votes MAMT 61 is shown in FIG. 5 above the distributed device revocation system keying material for an autonomous device node 55 and is called PM.

Computation of a revocation vote MAMT is as follows. This MAMT authenticates the revocation vote or information a device has. The revocation vote MAMT for device i has s+1 leaves $Lr_i^k$ for k=0, . . . , s. Each leaf is calculated as $Lr_i^k$=h (k||$R_i^k$). The root for the revocation vote MAMT for device i is called $RM_i$. The revocation vote MAMT 62 is shown in FIG. 5 to the right of the revocation values 60.

The second main stage of the keying material generation is generation of the global MAMT's 56, 57. The global partial revocation votes MAMT, denoted GPM 56, authenticates the partial revocation votes of network device nodes. GPM has n leaves having values $Lga_i$=h(i||$RAT_i$) for i=1, . . . , n. The global revocation votes MAMT, denoted GRM 57 (also sometimes called the global revocation vote authentication tree (GRCT)), authenticates the revocation votes of all network device nodes. GRM has n leaves having values $Lgc_i$=h (i||$RCT_i$) for i=1, . . . , n, where $RCT_i$ denotes the revocation vote authentication tree for device i.

With continuing reference to FIGS. 2 and 5, as part of the nodes setup 40 the setup server distributes to each autonomous device node the following distributed device revocation system keying material: (i) the distributed device revocation system keying material 55 for the autonomous device node including the set of t random revocation votes $\{r_{i,j}\}$, j= 1, . . . , t and the set of t hash revocation votes or hash chains $\{m_{i,j}^k\}$, j=1, . . . , t, k=1, . . . , s generated from the random revocation votes; (ii) the partial revocation votes MAMT 61 associated with the set of random revocation votes and hash chains; (iii) the revocation vote MAMT 62 associated with the revocation vote or information generated from the random revocation votes and the hash revocation votes; (iv) the path of the GPM 56 that enables device node i to authenticate both the random revocation votes and the hash revocation votes; and (v) the path of the GRM 57 that enables authentication of the revocation vote.

With reference to FIG. 2, in the network establishment operation 42 each device node discloses to its neighbor device nodes sufficient revocation information to enable the neighbor device nodes to collaborate to effectuate revocation of the device node. This disclosure is a prerequisite to joining the distributed network. Each neighbor device node receives partial revocation information for the current revocation session that are chosen between the t possible partial revocation votes for session k, namely $\{m_{i,j}^{s-k}\}$j=1 . . . t. The disclosed information are different for each neighboring device node. For example if t=8, x=2, current session is 5, and device node #7 has four neighbors, then device node #7 could disclose $\{m_{7,0}^{s-5}, m_{7,1}^{s-5}\}$, $\{m_{7,2}^{s-5}, m_{7,3}^{s-5}\}$, $\{m_{7,4}^{s-5}, m_{7,5}^{s-5}\}$, and $\{m_{7,6}^{s-5}, m_{7,7}^{s-5}\}$ to the first, second, third and fourth neighbor device nodes, respectively. Each neighbor device node further receives partial revocation votes MAMT and GPM 56 values that authenticate the partial revocation votes that a device node discloses to a neighbor device node. Each neighbor device node also receives revocation vote MAMT 62 and global revocation votes MAMT (GRM) 57 values that authenticate the revocation vote for current revocation session k. Note that these values are not enough for any single neighbor device node to revoke a suspect device node, as the revocation vote for the node is not disclosed. The revocation vote can only be generated by collaboration amongst the neighbor device nodes through sharing of the disclosed partial revocation vote information.

With continuing reference to FIG. 2, once the network is established by the operations 40, 42, it operates to perform its intended functionality, such as the medical monitoring and therapy functionality of the example medical distributed network 8 depicted diagrammatically in FIG. 1. During such operation, various autonomous device nodes intercommunicate by sending secured messages to one another. During a revocation session 70, each autonomous device node monitors its communications with other device nodes with the objective of detecting a suspect nature or behavior on the part of another device node that might suggest that the other device node is a suspect autonomous device node that may have been compromised in some way. Some examples of suspect nature or behavior may include, for example: sending a manifestly incorrect datum value; requesting an unauthorized service or operation; refusal to respond to an authorized request; improper or unexpected response to an authorized request; communication using invalid security information; or so forth. Each device node thus makes an individual decision during the revocation session 70 as to whether to vote to revoke a suspect node. To vote for revocation, the device node discloses its partial revocation information against the suspect node to other device nodes.

With continuing reference to FIG. 2, at any time during the revocation session 70, the device nodes can vote as to whether to exclude a suspect device node. In general, the vote to revoke takes place when all partial revocation votes against a suspect device have been disclosed. At a decision 74, it is decided whether the vote satisfies a revocation criterion, such as disclosure of all partial revocation votes against a suspect device. If not, then the revocation session 70 continues until its time interval expires. At expiration of the revocation session, any disclosed partial revocation votes are discarded 76 and a new revocation session begins. The revocation criterion can, for example, be a threshold criterion based on the number of votes in favor of removing the suspect autonomous device node. For example, if there are T distributed partial revocation votes for the suspect device, then T device nodes must vote in favor of revocation for the decision 74 to be in favor of revocation. In other embodiments, a majority-rule criterion is used, that is based on a ratio of votes in favor of revocation compared with the total number of autonomous device nodes. In the majority-rule approach, as more nodes are added the threshold T for revocation increases. Other revocation criteria can be used as well.

In some embodiments, a node trustworthiness weighting 78 is incorporated into the revocation criterion. The node trustworthiness embodied in the node trustworthiness weighting 78 is unrelated to whether the suspect device node has exhibited suspect behavior, and instead relates to intrinsic aspects of the device node that may make it more or less trustworthy. These intrinsic aspects may include, for example, commonality or difference of the suspect device node from other device nodes of the distributed network, under the assumption that a very different device node is more likely to be a compromised node, perhaps introduced by a nefarious third party to gain access to the distributed network. For example, if a device node for performing a non-medical function is introduced into the medical distributed network 8 of FIG. 1, it would be reasonable to assign such a non-medical device node a value for the node trustworthiness weighting 78 that indicates that the device node should not be readily trusted.

Another intrinsic aspect of the device node that may affect the assigned node trustworthiness weighting 78 is whether the suspect device node is configured to communicate with devices outside of the distributed network, under the assumption that such outside communication provides opportunities to compromise the suspect device node. Considering again the medical distributed network 8 of FIG. 1, if the ceiling-mounted external display monitor 22 is connected with the outside hospital network or with the Internet, then it would be reasonable to assign the display monitor 22 a value for the node trustworthiness weighting 78 that indicates that the device node should not be readily trusted. In contrast, if the chest-mounted sensor nodes 12, 14, 16 intercommunication only with other device nodes of the distributed network 8, then it would be reasonable to assign these sensor nodes 12, 14, 16 values for the node trustworthiness weighting 78 that indicates that these device node are more readily trusted.

Another intrinsic aspect of the device node that may affect the assigned node trustworthiness weighting 78 is the type of autonomous control or operating system the suspect autonomous device node is running. If the operating system is of a variety that is less secure and more readily compromised, then it would be reasonable to assign such a device node a value for the node trustworthiness weighting 78 that indicates that the device node should not be readily trusted. In contrast, if the operating system is of a variety that is considered more secure and difficult to compromise, then it would be reasonable to assign such a more intrinsically secure device node a value for the node trustworthiness weighting 78 that indicates that the device should be more readily trusted.

The various factors that impact the node trustworthiness weighting 78 can have different effects on the overall node trustworthiness weighting 78. For example, improper requests for information may weight heavily against node trustworthiness, whereas a measurement output that is out of range may weigh less heavily against node trustworthiness. In some embodiments, the effect of each of the various factors on the trustworthiness of a node are stored in a database at each node, or at a central server.

Figure 6:
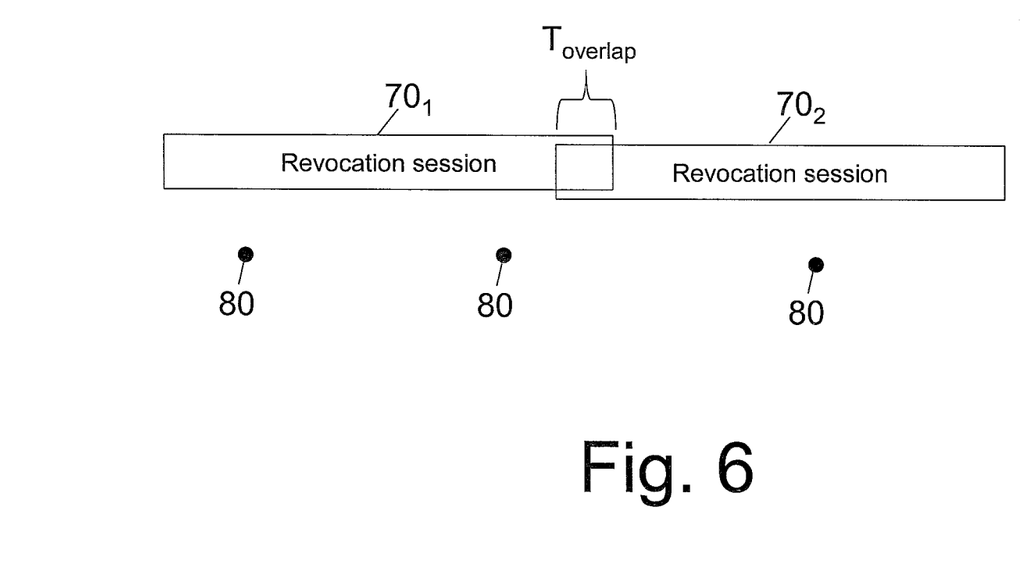
FIG. 6 diagrammatically shows relative timing for two neighboring revocation sessions.

FIG. 6 diagrammatically shows an example that illustrates an advantage of using the described revocation session approach. In FIG. 6, each occurrence of suspect aberrant behavior by a suspect node is indicated by a black dot 80. In a first revocation session 70₁, two such suspect events 80 occur, causing two neighboring device nodes to individually decide to revoke the suspect device node (assuming the two suspect events are observed by two different neighboring device nodes). These two device nodes vote individually for revocation, but are outvoted by the remaining device nodes that have observed no suspect behavior. As the collective vote was against revocation. At the termination of the first revocation session $70_1$, the two individual decisions in favor of revocation are discarded. A second revocation session $70_2$ begins at about the end of the first revocation session $70_1$.

In FIG. 6, the second revocation session $70_2$ temporally overlaps the first revocation session $70_1$ by a small time interval $T_{overlap}$ (that is, small respective to the duration of the revocation sessions $70_1$, $70_2$). If the next revocation session starts exactly starts when previous revocation session ends, this could lead to protocol malfunctions, for example if a revocation procedure is launched at the end of a revocation session but the revocation message (which is only valid for that revocation session) only reaches the rest of the network sometime in the next revocation session. By providing the temporal overlap $T_{overlap}$ of adjacent revocation sessions, this potential abnormal termination of a revocation procedure is eliminated or made less likely. During the overlap time interval $T_{overlap}$, the revocation procedure works according to the following rules: (i) members of the distributed network cast partial votes against nodes being revoked using partial revocation votes from the newest revocation session (that is, revocation session $70_2$ for the overlap time interval $T_{overlap}$ of FIG. 6); but, (ii) a node can receive and authenticate a combined revocation vote from either the newest revocation session (session $70_2$ in FIG. 6) or from the previous revocation session (session $70_1$ in FIG. 6)—the suspect node is revoked upon authentication in either case. Although the overlap time interval $T_{overlap}$ has certain advantages, it is contemplated to have no overlap, i.e. $T_{overlap}=0$.

With continuing reference to FIG. 6, during the second revocation session $70_2$ a single suspect event is observed, causing a single neighboring device node to individually decide to revoke the suspect device node. In the voting of the revocation session $70_2$, therefore, the collective vote is again against revocation. Without using revocation sessions, the effect would be that the votes for revocation would accumulate over time eventually leading to revocation of the suspect device node. Such a result is undesirable, because a properly functioning device node that has not been compromised may nonetheless occasionally exhibit behavior deemed suspect by a neighboring node, such as an occasional glitch that causes a manifestly invalid datum output or so forth.

Although the use of revocation sessions is typically advantageous, in some embodiments revocation sessions may be omitted and revocation votes allowed to accumulate over an extended time. In another variant, rather than simply discarding disclosed partial revocation votes at the end of a revocation session, those partial revocation votes may be used to adjust the node trustworthiness weighting 78. For example, if several nodes vote to revoke a suspect node by disclosing their partial revocation votes, but not enough uncompromised nodes vote to revoke to initiate the revocation operation, the existence of several disclosed partial revocation votes against the suspect device node may be used to adjust the node trustworthiness weighting 78 of the suspect device node. This approach reflects the fact that these partial revocation vote disclosures indicate that something may be problematic with the suspect node, even if the accumulated vote over the revocation session is not enough to revoke the suspect node.

With returning reference to FIG. 2, if at the decision 74 it is decided that the vote satisfies the revocation criterion, then the device nodes collaborate in an operation 84 to combine the disclosed partial revocation information relating to the revoked suspect device node to construct a revocation message (e.g., to reconstruct the revocation vote stored at the revoked suspect device node). The constructed revocation message is then intercommunicated across the distributed network in an operation 86, and each device node that receives the revocation message ceases communication with the revoked suspect device node. The effect of this intercommunication 86 is to exclude the revoked suspect device node from the distributed network. Optionally, the revocation message may include additional information beyond that need to authenticate the revocation message, such as a listing or identification of the observed aberrant behavior to assist in subsequent diagnosis by a human technician.

Optionally, the revocation message is communicated to a central control node responsive to contact with the central control node by at least one autonomous device node of the distributed network (typically other than the suspect autonomous device node) that has received and authenticated the revocation message. The central control node may optionally take further action, such as notifying human personnel of a potential security problem relating to the revoked suspect device node, or taking measures to ensure that the revoked suspect device node does not join other distributed networks, revoking associated keys, or so forth. In some embodiments, it is contemplated for the central controller to optionally reconfigure and readmit the suspect node back into the network. Such readmission is optionally conditional upon observation of the subsequent behavior of the suspect node, and may involve assigning a lower trust factor to the readmitted node.

The operations 84, 86 constitute the device node revocation phase, and only take place if it is determined by the voting decision 74 that a suspect device node is to be revoked. In this case, neighbor nodes of the suspect device node launch the revocation procedure 84, 86 against it. To this end, the neighbor device nodes exchange the partial revocation votes that they received from the suspect device node during the network establishment phase 42 and that they authenticated using both RAT and GRAT values. At the moment all the t partial revocation votes $(m_{i,1}^{s-k}, m_{i,2}^{s-k}, \ldots, m_{i,t}^{s-k})$ for revocation session k have been disclosed, any neighbor device node of the revoked suspect device node can compute the revocation vote against it by calculating the hash of the t well-arranged partial revocation votes for current session $k(R_i^k = h(m_{i,1}^{s-k} \| m_{i,2}^{s-k} \| \ldots \| m_{i,t}^{s-k}))$. To authenticate the computed revocation vote or information so as to verify the authorization to revoke the suspect device node, neighbor device nodes broadcast the computed revocation vote together with the values of both revocation vote authentication tree (RCT) and the global revocation vote authentication tree (GRCT) that authenticate this revocation vote.

The distributed device revocation system can also be used to provide key revocation when combined with a current key distribution system. The approach for revocation of a compromised key suitably depends upon the type of key pre-distribution scheme (KPS) used. For a random KPS, key revocation can be effectuated by deleting the compromised keys. For instance, once a group of device nodes vote to revoke a suspect device node and have launched the revocation procedure 84, 86 against it, all device nodes in the distributed network can delete the common keys with the revoked device node. However, this approach leads to a decrease in the number of secure links and reduces the connectivity of the network. To avoid this problem compromised keys are optionally updated instead of deleted. In deterministic KPS based on Blundo's polynomials, such as the HDP-KPS approach, keying material cannot be deleted since such deletion would cause a substantial decrease in network connectivity. Key revocation in this type of key distribution scheme optionally updates compromised keying material once a device has been compromised. This approach involves the collaboration of a secure setup server or central control node.

The voting in a key revocation system can be biased based on a trust factor indicative of trustworthiness of the suspect distributed key, in a manner similar to the way the node trustworthiness weighting 78 is used. Here, the individual decision to vote for revocation by an individual autonomous device node is suitably based on suspicious usages of the suspect distributed key. The collective voting on whether to revoke a distributed key can be based on a trust factor whose value is related to the length of the suspect distributed key or other security level-indicative characteristic of the key, or whose value is related to the trustworthiness of a device node that issued the distributed key, or so forth.

Existing KPS schemes are sensible to compromise by node replication, sybil attacks, or so forth. Examples can be found in a key pre-distribution schemes based on the random distribution of keys or on Blundo's polynomials. In random KPS an attacker can use keying material from several device nodes to make new ones and therefore an attacker can forge new identities. In KPS based on Blundo's polynomials an attacker can forge may identities by capturing a number of devices larger than a threshold number for successful compromise, and then reading the keying material out and reconstructing the keying material. The distributed device revocation approaches disclosed herein can be used to avoid such replication attacks. This avoidance results because the distributed device revocation system keying material cannot be replicated or forged since the partial revocation votes are randomly generated and only known by each receiving device node. Moreover, the partial revocation votes can be authenticated by using MAMT. Accordingly, the distributed device revocation approaches disclosed herein avoid identity falsification as the keying information of the distributed device revocation system cannot be reconstructed.

In the medical distributed network 8, suspect nature or behavior is detected and can, upon a suitable voting result, result in revocation of the suspect device node. This suspect nature or behavior in the medical distributed network 8 typically relates to a perceived or actual security threat in which the suspect device node is perceived to, or actually has been, compromised by an intruder, for example through the intermediary of a digital virus, Trojan horse, worm, or other malicious software or executable digital code. However, more generally, "suspect" nature or behavior of the suspect autonomous device node is to be broadly construed as any characteristic or behavior that is deemed contrary to the welfare or purposes of the distributed network.

For example, another contemplated application of the disclosed distributed device revocation approaches disclosed herein is in a peer-to-peer file sharing network, such as an Internet-based peer-to-peer music sharing network, peer-to-peer movie sharing network, or the like. In such an application, suspect behavior may include attempts to share (that is, send, offer to send, or solicit) copyrighted material in violation of applicable copyright laws or ethical considerations. For example, each legitimate autonomous node (such as a personal computer, portable music player, Internet-capable stereo or entertainment system, or other consumer music device) may maintain a list of copyrighted songs. If a legitimate autonomous device node is contacted by another autonomous node that either solicits or offers to send a song that is on the legitimate autonomous node's list of copyrighted songs, then the legitimate autonomous node suitably makes the individual decision that the other autonomous node is a suspect autonomous node whose access privileges on the peer-to-peer sharing network should be revoked.

Note that this individual decision does not necessarily involve human intervention—rather, the legitimate autonomous node may detect the solicitation or offer to send, recognize it relates to a copyrighted song, and reject the offer and log the individual decision to revoke without any human intervention. Alternatively, human intervention can be solicited, for example by displaying the request and asking a human user for a decision as to whether to follow up with a vote to revoke.

In the contemplated distributed peer-to-peer file sharing application, the peer-to-peer network occasionally holds a revocation session in which the autonomous device nodes presently online (presumed to be mostly legitimate autonomous nodes, that is, operated by law-abiding users) vote on revocation of suspect autonomous nodes (suitably defined here as any autonomous node for which there is at least one individual vote to revoke privileges). Again, this voting is typically automated, although optionally a human user is first asked to authorize participation, or is asked to authorize a particular vote to revoke, or is otherwise requested to intervene.

By taking a vote of those autonomous device nodes that are presently online on the peer-to-peer network, it is ensured that a legitimate node cannot be revoked arbitrarily by a single online autonomous node; rather, such a revocation can only be the result of a vote in which a substantial number of presently online autonomous nodes vote for revocation, indicating that the suspect autonomous node is likely to be a repeat copyright offender. Moreover, other optional provisions set forth herein may optionally be applied. For example, the revocation session concept can be incorporated by making individual decisions to revoke expire after a certain time period to avoid revocation of a legitimate user's privileges due to accumulation over several years of a few inadvertent improper song requests. However, since in a peer-to-peer network the fraction of available device nodes actually online at the time of voting may be low, it may be advantageous to retain individual votes to revoke over two or more revocation sessions to increase the persistence of such individual votes. Similarly, weighting based on trustworthiness can be employed, based on suitable criteria such as a probation status suitably assigned to previous offenders who have been readmitted to the peer-to-peer network on a probational basis. The revocation message optionally includes additional information beyond that sufficient to authenticate the revocation message, such as a detailed list of the observed alleged or apparent copyright violations that formed the basis for the revocation, so as to enable the alleged copyright infringer to review the evidence and appeal the revocation if desired (for example, before a human reviewer).

In such a peer-to-peer file-sharing network application, the concept of "suspect" nature or behavior may extend beyond copyright violation behavior to other aspects, such as sharing or attempting to share a file detected as containing a virus, or overuse of the file-sharing network, or so forth. Moreover, while revocation of suspect device nodes is described, the approach can also be used to revoke suspect distributed keys that are not associated with a particular device node. For example, the suspect distributed key may be the digital signature associated with a song.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A distributed revocation method comprising:
   conducting a vote amongst at least three autonomous device nodes of a distributed network regarding whether a suspect autonomous device node of the distributed network should be removed from the distributed network;
   responsive to said vote satisfying a revocation criterion, ceasing communication between the suspect autonomous device node and the other autonomous device nodes of the distributed network by (i) constructing a revocation message by combining partial revocation information for revoking the suspect autonomous device node that is distributed amongst at least some of the autonomous device nodes of the distributed network other than the suspect autonomous device node, and (ii) transmitting the revocation message amongst the autonomous device nodes over the distributed network; and
   authenticating the revocation message by comparing a first portion of the revocation message processed by a one-way function with a second portion of the revocation message.

2. The distributed revocation method as set forth in claim 1, further including:
   forwarding the revocation message to other autonomous device nodes in other distributed networks.

3. The distributed revocation method as set forth in claim 1, further including:
   authenticating the revocation message received at an autonomous device node by comparing a first portion of the revocation message processed by a hash function with a second portion of the revocation message.

4. The distributed revocation method as set forth in claim 1, further including:
   incorporating a new autonomous device node into the distributed network responsive to transferal of partial revocation information for the new autonomous device node from the new autonomous device node to a plurality of autonomous device nodes already in the distributed network.

5. The distributed revocation method as set forth in claim 1, wherein the voting is weighted based on a trust factor indicative of trustworthiness of the suspect autonomous device node in the distributed network.

6. The distributed revocation method as set forth in claim 1, wherein the voting recurs over temporally limited revocation sessions, and votes in previous revocation sessions do not count in subsequent revocation sessions.

7. The distributed revocation method as set forth in claim 1, further including:
   performing a plurality of medical functions using at least some of the autonomous device nodes of the distributed network.

8. A distributed network comprising:
   a plurality of autonomous device nodes each configured to securely communicate with other autonomous device nodes to define the distributed network and to cooperate with other autonomous device nodes with which it is in secure communication to perform the distributed revocation method of claim 1.

9. A non-transitory digital medium carrying software which controls a processor to perform the method of claim 1.

10. An autonomous device node configured to securely communicate with other autonomous device nodes in a distributed network and to cooperate with other autonomous device nodes with which it is in secure communication to perform a distributed revocation method including (i) conducting a vote amongst at least three autonomous device nodes of a distributed network regarding whether a suspect autonomous device node of the distributed network should be removed from the distributed network, and (ii) ceasing communication with the suspect autonomous device node responsive to said vote satisfying a revocation criterion; and
   data storage for storing partial revocation information for other autonomous device nodes, the autonomous device node being further configured to cooperate with other autonomous device nodes to combine partial revocation information for the suspect autonomous device node stored in the data storage with partial revocation information for the suspect autonomous device node stored at other autonomous device nodes to construct a revocation message that is transmitted amongst the autonomous device nodes on the distributed network to effectuate ceasing of communication with the suspect autonomous device responsive to said vote satisfying the revocation criterion, wherein the revocation message received at each autonomous device node is authenticated by comparing a first portion of the revocation message processed by a one-way function with a second portion of the revocation message.

11. The autonomous device node as set forth in claim 10, further including:
    data storage for storing complete revocation information, the autonomous device node being further configured to perform a distributed network joining method that includes communicating partial revocation information derived from the complete revocation information to a plurality of other autonomous device nodes, the partial revocation information communicated to each other autonomous device node being (i) insufficient by itself to reconstruct the complete revocation information but (ii) combinable with the partial revocation information communicated to the other autonomous device nodes to reconstruct the complete revocation information.

12. The autonomous device node as set forth in claim 10, wherein the vote is weighted based on a trust factor indicative of trustworthiness of the suspect autonomous device node in the distributed network.

13. A distributed revocation method comprising:
    conducting a temporally limited revocation session at which individual decisions of a plurality of autonomous device nodes are combined to decide whether a suspect autonomous device node should be removed from the distributed network;
    constructing a revocation message from revocation information previously distributed across at least some of the autonomous device nodes of the distributed network;
    transmitting the revocation message amongst the autonomous device nodes over the distributed network other than the suspect autonomous device node; and
    authenticating the revocation message the autonomous device nodes by comparing a first portion of the revocation message processed by a one-way function with a second portion of the revocation message; and
    removing the suspect autonomous device node from the distributed network responsive to the authenticated revocation message.

14. The distributed revocation method as set forth in claim 13, further comprising:
    repeating the conducting of the revocation session for subsequent revocation sessions that overlap temporally.

15. The distributed revocation method as set forth in claim 13, further comprising:
    repeating the conducting of the revocation session for subsequent revocation sessions.

16. The distributed revocation method as set forth in claim 15, further including:
    discarding the individual decisions made during a revocation session when said revocation session expires.

17. The distributed revocation method as set forth in claim 13, wherein the removing of the suspect autonomous device node from the distributed network further includes:
    authenticating the revocation message at each autonomous device node other than the suspect autonomous device node that receives the revocation message; and
    ceasing communication between the suspect autonomous device node and the revocation message-receiving autonomous device node responsive to successful authentication of the received revocation message.

18. The distributed revocation method as set forth in claim 13, further including:
    incorporating a new autonomous device node into the distributed network responsive to distribution of revocation information for the new autonomous device node across at least some of the autonomous device nodes already in the distributed network.

19. The distributed revocation method as set forth in claim 13, wherein the conducting of the revocation session includes:
    biasing the decision based on a trust factor indicative of a trustworthiness of the suspect autonomous device node.

20. An autonomous device node configured to securely communicate with other autonomous device nodes in a distributed network and to cooperate with other autonomous device nodes with which it is in secure communication to perform the distributed revocation method as set forth in claim 13.

21. In a distributed medical monitoring network, a plurality of nodes, each node programmed to:
    communicate and conduct a vote with other nodes of the network whether to revoke network communication with a node detected engaging in one or more suspicious activities;
    construct a revocation message by combining partial revocation information for revoking the suspect node that is distributed amongst the other nodes of the network other than the suspect node, and
    transmit the revocation message amongst the plurality of nodes of the network, the revocation message including a first portion and a second portion,
    authenticate the revocation message by comparing a first portion of the revocation message processed by a one-way function with a second portion of the revocation message,
    cease communication with the suspect node responsive to said vote satisfying a revocation criteria.

22. The plurality of nodes as set forth in claim 21, further comprising:
    a database storing the effect of each of a plurality of factors on a node trustworthiness, the communicating and voting being biased by trustworthiness of the node detected engaging in the one or more suspicious activities computed based on the factors stored in the database.

23. A distributed network comprising a plurality of nodes, each node configured to:
    (i) randomly generate and transmit to other nodes partial revocation votes combinable to construct a revocation message against the node such that the partial revocation vote distributed to one other node cannot be replicated or forged by another node; the revocation message including a first portion and a second portion; and
    (ii) store partial revocation votes received from other nodes;
    (iii) communicate and conduct a vote with other nodes of the network whether to revoke network communication with a node detected engaging in one or more suspicious activities;
    (iv) authenticate the revocation message by processing one of a first and second portions of the revocation message processed by a one way function;
    (v) cease communication with the suspect node responsive to said vote satisfying a revocation criteria.

24. The distributed network as set forth in claim 23, wherein the nodes comprise members of a peer-to-peer file sharing network.

25. The distributed network as set forth in claim 24, wherein each node further includes:

a list of copyrighted files, each node configured to disclose its partial revocation vote against another node responsive to detection of trafficking by the other node in a file included in the list of copyrighted files.

26. The distributed network as set forth in claim 23, wherein the nodes comprise members of a distributed medical monitoring network, and each node is configured to disclose its partial revocation vote against another node responsive to detection of suspicious activity by the other node.

\* \* \* \* \*